(12) United States Patent
Ishima et al.

(10) Patent No.: US 7,718,607 B2
(45) Date of Patent: May 18, 2010

(54) METHOD OF PRODUCING S-NITROSOPROTEIN PREPARATION

(75) Inventors: Yu Ishima, Kumamoto (JP); Takaaki Akaike, Kumamoto (JP); Masaki Otagiri, Kumamoto (JP)

(73) Assignee: NIPRO Corporation, Osaka (JP)

( * ) Notice: Subject to any disclaimer, the term of this patent is extended or adjusted under 35 U.S.C. 154(b) by 0 days.

(21) Appl. No.: 12/218,059

(22) Filed: Jul. 11, 2008

(65) Prior Publication Data

US 2008/0287655 A1  Nov. 20, 2008

Related U.S. Application Data (62) Division of application No. 11/890,542, filed on Aug. 7, 2007.

(30) Foreign Application Priority Data

Aug. 24, 2006 (JP) .............................. 2006-227427

(51) Int. Cl.
*A61K 38/00* (2006.01)
*A07K 14/00* (2006.01)
(52) U.S. Cl. ............................ 514/2; 530/350; 530/409
(58) Field of Classification Search ...................... 514/2; 530/350, 409
See application file for complete search history.

(56) References Cited

U.S. PATENT DOCUMENTS 3,992,367 A   11/1976   Plan et al. ................... 260/122
5,118,794 A    6/1992   Grangeorge et al. ......... 530/363
6,617,133 B1   9/2003   Noda et al. ................ 435/69.6
2005/0222026 A1 10/2005 Otagiri et al. .................. 514/12

FOREIGN PATENT DOCUMENTS

JP    2005-206577 A    8/2005
WO    98/29452 A1      7/1998
WO    98/43621 A1     10/1998

OTHER PUBLICATIONS

Gandley et al., Hypertension 45, 21-27 (2005).*
Ignarro, Louis J., "Endothelium-Derived Nitric Oxide: Pharmacology and Relationship to the Actions of Organic Nitrate Esters", *Pharmaceutical Research*, vol. 6, No. 8, 1989, pp. 651-659.
Ignarro, Louis J. et al., "Mechanism of Vascular Smooth Muscle Relaxation by Organic Nitrates, Nitrites, Nitroprusside and Nitric Oxide: Evidence for the Involvement of S-Nitrosothiols as Active Intermediates", *The Journal of Pharmacology and Experimental Therapeutics*, vol. 218, No. 3, 1981, pp. 739-749.

* cited by examiner

*Primary Examiner*—Chih-Min Kam
(74) *Attorney, Agent, or Firm*—Kubovcik & Kubovcik (57) ABSTRACT

A protein is efficiently nitrosylated with nitrogen monoxide by merely mixing S-nitrosoglutathione as a nitrogen monoxide donor with a protein solution containing a stabilizing agent comprising at least one compound or a combination of plural compounds selected from an N-acetylamino acid, a fatty acid, and a fatty acid salt. The method that enables efficient NO addition to a cysteine residue in un-nitrosylated protein without changing the structure of protein and hence provides NO to a living organism.

5 Claims, 6 Drawing Sheets

METHOD OF PRODUCING S-NITROSOPROTEIN PREPARATION

This application is a division of U.S. patent application Ser. No. 11/890,542 filed Aug. 7, 2007, which claims priority of Japanese Patent Application No. 2006-227427, filed Aug. 24, 2006, which is incorporated herein by reference.

TECHNICAL FIELD

The present invention relates to an S-nitrosoprotein preparation containing a stabilizing agent and to a production method therefor. More specifically, the present invention relates to an S-nitrosoprotein preparation containing nitrogen monoxide which is efficiently produced by merely mixing S-nitrosoglutathione as a nitrogen monoxide donor with a protein solution containing a stabilizing agent.

BACKGROUND ART

Nitrogen monoxide (hereinafter abbreviated as NO) has been widely studied in various fields such as applications to control physiological functions, clinical episodes, and therapy. In particular, in ischemic disorders or at the time of organ transplantation, various disorders are caused by endogenous reduction in NO production due to substrate depletion accompanying blood flow decrease, so that exogenous NO supplementation (called NO supplementation therapy) is indispensable. Although among others NO inhalation therapy has been tried as the NO supplementation therapy, the current situation is that NO disappears in an extremely short time in a living organism and selective obtention of advantageous effects is difficult because of NO itself having high reactivity and diversity (Ignarro L. J. et al., Pharm Res., 1989, 6, 651-659).

NO is known to react, in a living organism, with a thiol group (hereinafter, abbreviated as an SH group) of a protein or the like and converted into S-nitrosothiol (hereinafter, abbreviated as RS-NO), which maintains a relatively stable state and functions as an NO reservoir, thus participating in control of NO concentration in the living organism (Ignarro L. J. et al., J. Pharmacol. Exp. Ther., 1981, 218 739-749).

Usefulness of nitrosylated proteins has been reported. Analyses on the efficiency of nitrosylation and antibacterial activity of various bacteria-infected model animals using albumin variants having a mutation in one or more amino acid residues in the constituent amino acid sequences indicated that the albumin variants are efficiently nitrosylated and the nitrosylated products exhibit more potent antibacterial activity than NO and low molecular weight nitrosothiol (JP 2005-206577 A, US2005/0222026).

On the other hand, albumin can be used as an NO transport protein. In spite of having a free cysteine residue at the 34th position, albumin is known to have only a low reactivity, so that attempts to allow albumin and an NO donor to react to promptly obtain S-nitrosylated albumin fail. Then, to add NO to albumin, a method is known in which the binding efficiency is increased by adding a suitable chemical modulator to albumin or the reaction efficiency is increased by mutating a part of amino acids of albumin to cysteine. These methods involve changing the inherent structure of albumin, which causes the problem that the behavior of albumin in the living organism may be changed.

DISCLOSURE OF THE INVENTION

It is an object of the present invention to provide a nitrosoprotein preparation and to provide a production method that enables efficient NO addition to a cysteine residue in an un-nitrosylated protein without changing the structure of the protein and hence to provide NO to a living organism.

The inventors of the present invention have made extensive studies with a view to achieving the above-mentioned object and as a result, they have found that addition of a stabilizing agent such as a fatty acid, fatty acid salt or N-acetylamino acid to a protein allows reaction of a thiol group of the protein with NO to provide S-nitrosoprotein, thus accomplishing the present invention. In particular, addition of a stabilizing agent such as a fatty acid, fatty acid salt or N-acetylamino acid to albumin permits reactivity of cysteine at the 34th position to be increased, allowing ready reaction of cysteine in the albumin with NO to provide S-nitrosoalbumin, thus accomplishing the present invention.

That is, the present invention provides:

(1) an S-nitrosoprotein preparation containing a stabilizing agent including at least one compound or a combination of compounds selected from an N-acetylamino acid, a fatty acid or a fatty acid salt;

(2) the S-nitrosoprotein preparation according to item (1), in which the N-acetyl amino acid is N-acetyltryptophane or N-acetylmethionine;

(3) the S-nitrosoprotein preparation according to item (1), in which the fatty acid is oleic acid or caprylic acid;

(4) the S-nitrosoprotein according to item (1), in which the fatty acid salt is sodium caprylic acid;

(5) a method of producing an S-nitrosoprotein preparation comprising adding a nitrogen monoxide donor to a protein solution containing a stabilizing agent including at least one compound or a combination of compounds selected from N-acetylamino acid, a fatty acid or a fatty acid salt;

(6) the production method according to item (5), in which the nitrogen monoxide donor is S-nitrosoglutathione;

(7) an improving agent for an ischemic disorder containing the S-nitrosoprotein preparation according to any one of items (1) to (4), in which the S-nitrosoprotein is S-nitrosoalbumin;

(8) an organ protecting agent for organ transplantation containing the S-nitrosoprotein preparation according to any one of items (1) to (4), in which the S-nitrosoprotein is S-nitrosoalbumin;

(9) a pharmaceutical composition containing the S-nitrosoprotein preparation according to any one of items (1) to (4), in which the S-nitrosoprotein is S-nitrosoalbumin; and (10) a pharmaceutical composition according to item (9), in which the pharmaceutical composition is obtained by mixing an albumin solution containing a stabilizing agent with a nitrogen monoxide donor from 24 hours before administration to just before administration.

The S-nitrosoprotein preparation of the present invention, which contains one or a combination of stabilizing agents selected from the group consisting of an N-acetylamino acids, a fatty acid, and a fatty acid salt, can increase the binding efficiency between an SH group in the protein and nitrogen monoxide, and increase stability. For example, when the protein is albumin, there occurs substantially no structural change and a stable S-nitrosothiol conformation can be obtained.

An S-nitrosoalbumin preparation serves as a donor of NO for various disorders caused by endogenous reduction in NO production due to substrate depletion accompanying a blood flow decrease in ischemic disorders or during organ transplantation, and protects ischemic site organ derived from activated oxygen species. Further, S-nitrosoprotein preparations can be expected to exhibit biological activities such as improvement of blood flow in liver tissue, suppression of neutrophil infiltration, neutrophil apoptosis activity, etc. Moreover, a protein, for example, albumin, undergoes substantially no structural change and hence is not recognized as a heterologous protein, so that the protein, for example, albumin, can be used safely in a human body.

In the present invention, nitrosylation means addition of a nitroso group (—NO) to a protein. Nitrosylation of the protein is preferably addition of a nitroso group to a thiol group in the protein, which can be achieved by a known method which involves reaction with a nitrogen monoxide donor such as nitrous acid salts, S-nitrosoglutathione (hereinafter, abbreviated as GSNO), S-nitrosocysteine, S-nitroso-N-acetyl-DL-penicillamine, or propylamine NONOate (diazoniumdiolate).

In the present invention, the protein to be nitrosylated is not particularly limited and commonly used proteins can be used. For example, any protein having a thiol group such as albumin, globulin, heparin, hemoglobin, or a1-antitrypsin may be used. Among these, albumin, globulin, and heparin that are present in blood are preferable. Proteins which are produced by genetic engineering may also be satisfactorily used. When used as a drug, those proteins derived from humans are preferable and in this case, the proteins may be either ones collected from individuals or ones produced by genetic engineering. Human-derived albumins are preferable irrespective of whether they are collected from individuals or produced by genetic engineering.

The stabilizing agent to be added to the protein of the present invention can be at least one compound or a combination of compounds selected from an N-acetylamino acid, a fatty acid and a fatty acid salt. Presence of the stabilizing agent enables nitrosylation in which nitrogen monoxide is added to, for example, the thiol group at the 34th position of the amino acid sequence of albumin and conversion of the protein into a protein that is stable after the nitrosylation.

The fatty acid or fatty acid salt to be added to the protein is not particularly limited and among those represented by the general formula $C_nH_{2n+1}COOH$, those represented by the general formula in which n=2 to 30 are preferable, more preferably, those represented by the general formula in which n=4 to 20, and more preferably, those represented by the general formula in which n=6 to 10, are suitable. Examples thereof include caprylic acid, caproic acid, and capric acid. Among these, caprylic acid is preferable. Fatty acid salts include sodium salts, potassium salts, etc. thereof.

The fatty acid(s) or fatty acid salt(s) or N-acetylamino acid(s) or combination thereof can be added to the protein in a concentration of 0.01 to 100 mM, preferably 0.1 to 50 mM, and more preferably 1 to 20 mM. The method of adding the fatty acid(s) or fatty acid salt(s) or N-acetylamino acid(s) or combination thereof to the protein is not particularly limited. The fatty acid(s) or fatty acid salt(s) or N-acetylamino acid(s) or combination thereof may be contained in the protein in advance or suitable amounts of the fatty acid(s) or fatty acid salt(s) or N-acetylamino acid(s) or combination thereof may be added to the protein. When the fatty acid(s) or fatty acid salt(s) or N-acetylamino acid(s) or combination thereof is (are) in a mixed state with the protein, a sufficiently good environment is provided for the nitrosylation of proteins.

N-acetylamino acid(s) contained as a stabilizing agent includes amino acid components such as N-acetyltryptophane and N-acethylmethionine.

Pharmaceutically acceptable excipients cause no problems in the nitrosylation and can be added to the S-nitrosoprotein preparation of the present invention.

In the nitrosylation, a thiol group of the protein is nitrosylated by adding a nitrogen monoxide donor for nitrosylation to a solution containing a stabilizing agent, for example, a caprylic acid, and a protein such as albumin.

The nitrogen monoxide donor includes a nitrous acid salt, a S-nitrosoglutathione (GSNO), an S-nitrosocysteine, an S-nitroso-N-acetyl-DL-penicillamine, and a propylamine NONOate. The GSNO is preferable.

When a protein is nitrosylated, the content of the nitrogen monoxide donor can be 0.01 to 50 mM, preferably 0.1 to 30 mM, and more preferably 1 to 10 mM.

The nitrosylation of a protein can be performed at a temperature of 4 to 40° C., preferably 15 to 40° C., and more preferably 25 to 37° C. for a time of 1 to 360 minutes, preferably 10 to 300 minutes, and more preferably 20 to 180 minutes.

Among proteins, a chemically non-modified albumin is nitrosylated at the thiol group at the 34th position of the amino acid sequence of the chemically non-modified albumin. In this case, the nitrosylation is performed under very mild conditions without an accompanying intermolecular cleavage of amino acids or an intramolecular cleavage of amino acids and, therefore, it is seldom the case that an original function or a steric structure of albumin is damaged.

For example, albumin has 17 sites where the thiol groups undergo intramolecular crosslinking and the nitrosylation can be performed in the presence of the stabilizing agent after the internal crosslinking is reductively cleaved.

When the S-nitrosoprotein of the present invention is S-nitrosoalbumin, S-nitrosoalbumin itself is effective to an ischemic reperfusion injury model and, therefore, can be used as an improving agent for ischemic diseases.

When the S-nitrosoprotein of the present invention is S-nitrosoalbumin, S-nitrosoalbumin itself has an anti-apoptosis effect or an induction activity for antioxidation and, therefore, can be used as an organ protecting agent at the time of organ transplantation.

The methods of administering the improving agent and the protecting agent of the present invention include oral administration, subcutaneous injection administration, and intravenous administration. However, the present invention should not be considered to be limited thereto.

The S-nitrosoprotein preparation of the present invention can be an S-nitrosoalbumin preparation and a pharmaceutical composition containing the S-nitrosoalbumin preparation can be formulated. Examples of the pharmaceutical composition include a composition that contains commonly used components constituting tablets such as an excipient, a lubricant, a binder and the S-nitrosoalbumin preparation of the present invention; a composition that contains commonly used components constituting an injectable agent, such as a solvent, a tonicity agent, a pH adjuster, and an antiseptic agent and the S-nitrosoalbumin preparation of the present invention.

Further, there may be exemplified a pharmaceutical composition that includes an albumin solution containing a stabilizing agent and a nitrogen monoxide donor which are separately packaged and mixed and adjusted during a period from 24 hours before administration to just before administration. That is, S-nitrosoalbumin is more stabilized than conventional one by at least one compound or a combination of plural compounds selected from N-acetylamino acids, fatty acids, and fatty acid salts, and S-nitrosoalbumin preparation can be supplied in a more stable state by formulating S-nitrosoalbumin as a pharmaceutical composition that can be mixed with a nitrogen monoxide donor and adjusted during a period from 24 hours before administration to just before administration. When albumin is nitrosylated without the stabilizing agent, the albumin is not nitrosylated (see, Comp. Ex. 2).

EXAMPLE

Reference Example 1

A 3 mM solution of a recombinant human serum albumin (hereinafter, abbreviated as HSA) solution containing 16.0 mM caprylic acid and 18.6 mM N-acetyltryptophane was measured for absorbance at a wavelength of 405 nm using 5,5'-dithiobis(2-nitrobenzoic acid) (DTNB) (hereinafter, abbreviated as DTNB method) to confirm the sensitivity of SH group of HSA. The result obtained is illustrated in FIG. 1.

Figure 1:
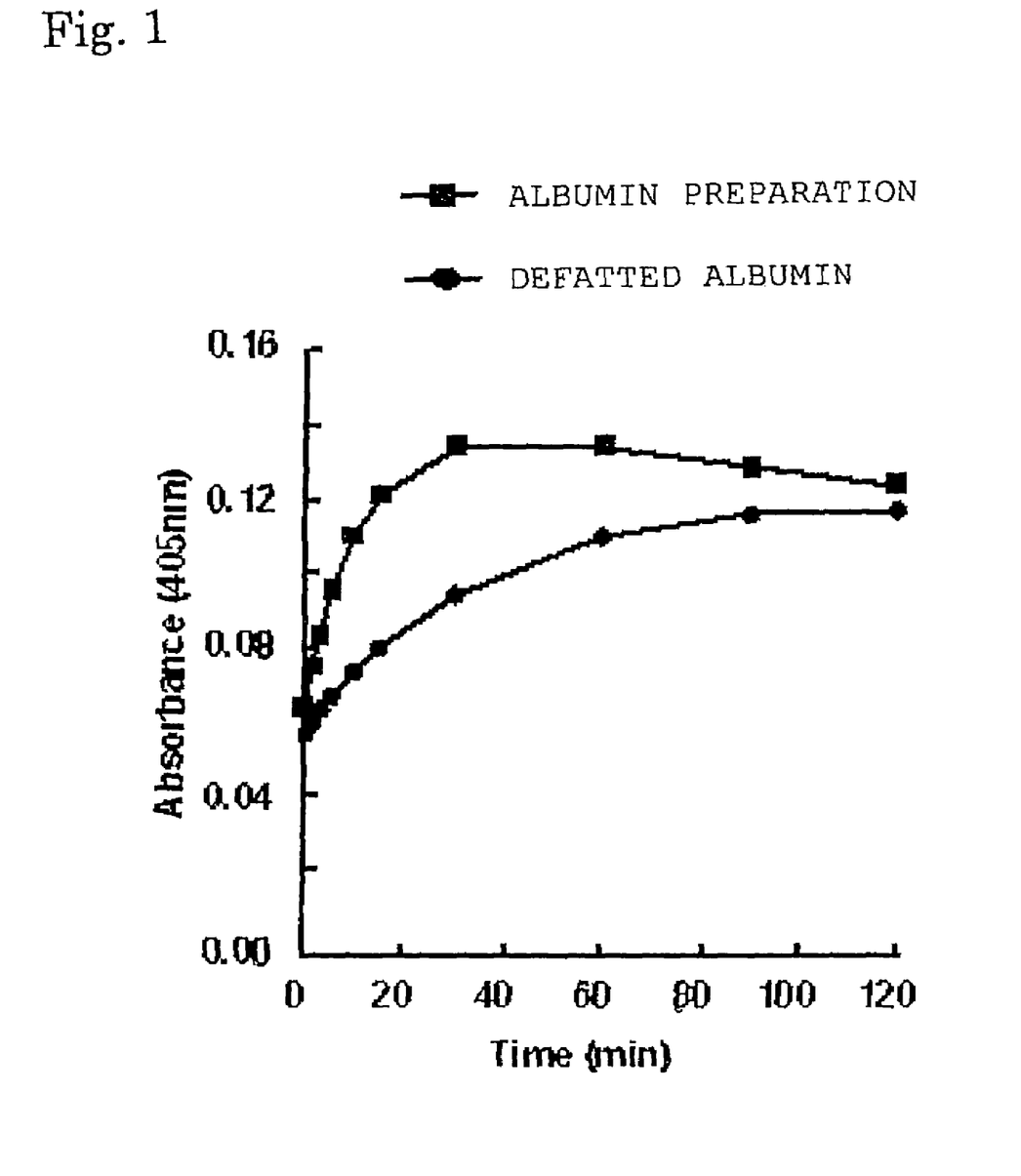
FIG. 1 is a graph illustrating change of SH group sensitivity in an HSA solution in the presence of a fatty acid versus time.

In FIG. 1 the ordinate axis indicates absorbance at 405 nm of 3-carboxy-4-nitrosothiophenolate ions liberated by the reaction of DTNB with an SH group.

As illustrated by the time line indicated by the symbol ■ in FIG. 1, in the case of the HSA solution, the reaction reached a plateau in about 30 minutes, which confirmed that the SH group of albumin in the HSA solution containing 16.0 mM caprylic acid had a high sensitivity.

Comparative Reference Example 1

To the HSA solution containing 16.0 mM caprylic acid and 18.6 mM N-acetyltryptophane activated carbon was added to obtain defatted albumin of the same concentration, which then was confirmed for sensitivity of the SH group in the same manner as that in Example 1. The result obtained is illustrated in FIG. 1.

As illustrated by the time line indicated by the symbol ●, in the case of defatted albumin, the absorbance increased moderately and did not reach a plateau even after 30 minutes.

Example 1

A 300 μM HSA solution containing 1.6 mM caprylic acid and 1.86 mM N-acetyltryptophane was prepared. To the HSA solution was added GSNO in an amount five times that of the HSA by mole ratio and the resultant was allowed to react at 37° C. for 1 minute to obtain an S-nitroso-HSA sample. Then, aliquots of sample were subjected to storage tests for 10 days under conditions of 4° C. with light shielding, 4° C. without light shielding, 25° C. with light shielding, and 25° C. without light shielding, respectively, and NO concentrations were measured with time by an HPLC-flow reaction system method using a Griess reagent to confirm the nitrosylated state of HSA.

Figure 2:
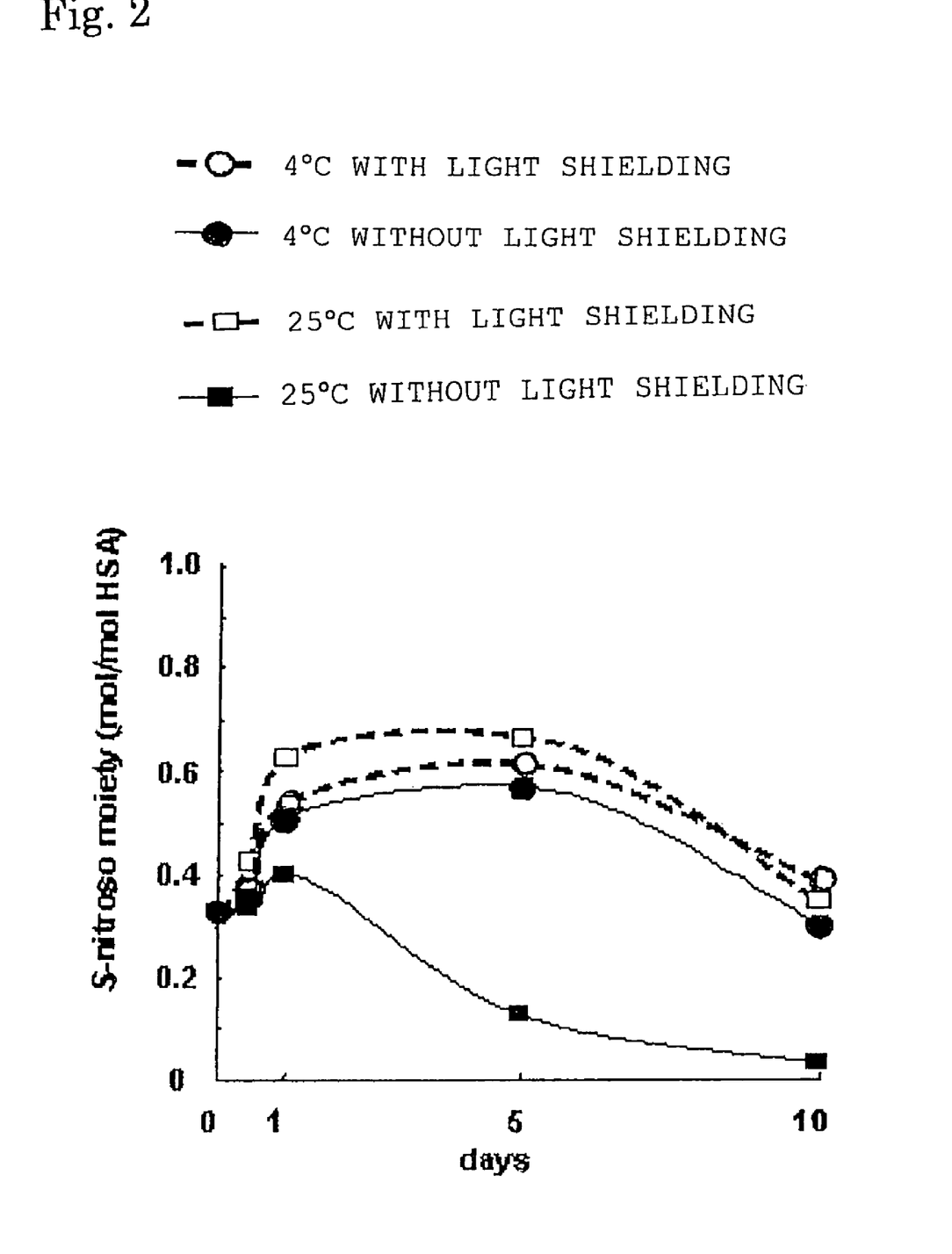
FIG. 2 shows a graph illustrating change of the NO addition rate versus time of an HSA solution when a nitroso-HSA sample was stored under various conditions.

The result obtained is illustrated in FIG. 2. The ordinate axis indicates S-nitroso moiety, that is, NO addition rate. The symbol ---○--- indicates a storage condition of 4° C. with light shielding; the symbol --●-- indicates a storage condition of 4° C. without light shielding; the symbol ---□--- indicates a storage condition of 25° C. with light shielding; and the symbol --■-- indicates a storage condition of 25° C. without light shielding. The ordinate axis indicates NO concentration per mol HSA.

While under the conditions of 4° C. with light shielding and 4° C. without light shielding, no great difference was observed in residual ratio of nitroso group, whereas disappearance of NO when stored at 25° C. was extremely rapid under the condition without light shielding as compared with the condition with light shielding. In this study, no removal operation for GSNO, that is, the NO donor, was performed, which would lead to a gradual increase in residual ratio until day 5.

Comparative Example 1

All the procedures of Example 1 were repeated except that a 300 μM HSA solution containing neither 1.6 mM caprylic acid nor 1.86 mM N-acetyltryptophane was used. As a result, without the need of checking stability, nitrosylation itself of HSA was not observed.

Example 2

A 300 μM HSA solution containing 1.6 mM caprylic acid and 1.86 mM N-acetyltryptophane was prepared. To this was added a 1.5 mM S-nitrosoglutathione (GSNO) solution and the resultant was mixed at 37° C. for about 30 minutes with light shielding to obtain an S-nitroso-HSA sample. Then, the sample was measured for NO concentration by an HPLC-flow reactor system method using a Griess reagent to confirm the nitrosylation of HSA.

Experimental Example 1

To confirm the structure of S-nitrosoalbumin obtained in Example 2, circular dichroic spectrum (hereinafter abbreviated as CD-spectrum) was measured (using a Jasco corporation J-720 Model spectropolarimeter). The results obtained are illustrated in FIG. 3 and FIG. 4.

Figure 3:
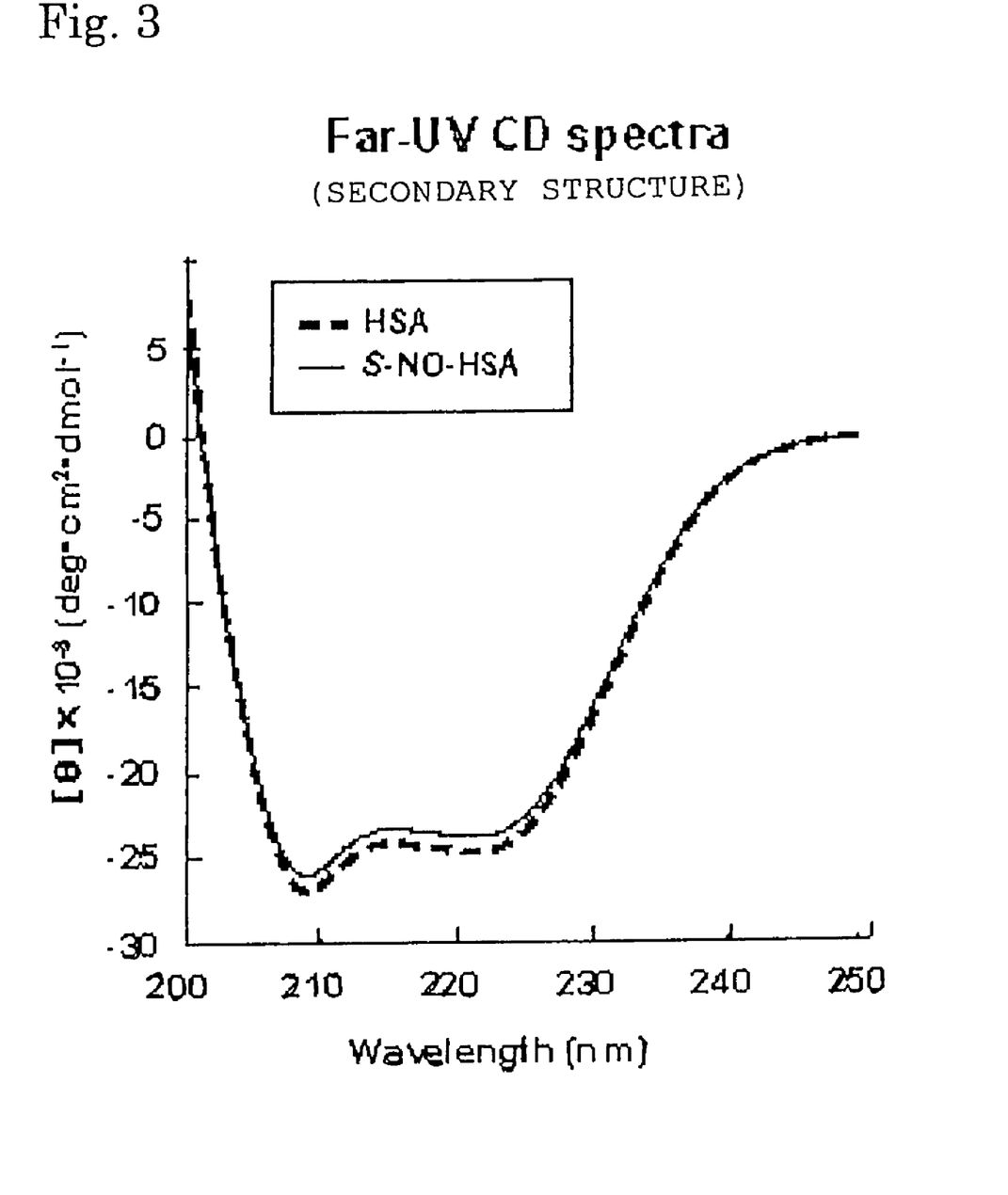
FIG. 3 is a graph illustrating the spectra of a nitroso-HSA sample in a far-ultraviolet region (Far-UV CD spectra).

In FIG. 3, the ordinate axis indicates [θ], that is, ellipticity per mole and the abscissa axis indicates wavelength. HSA indicated by a broken line indicates non-nitrosylated albumin and S-NO-HSA indicated by a solid line indicates nitroso-HSA sample.

Figure 4:
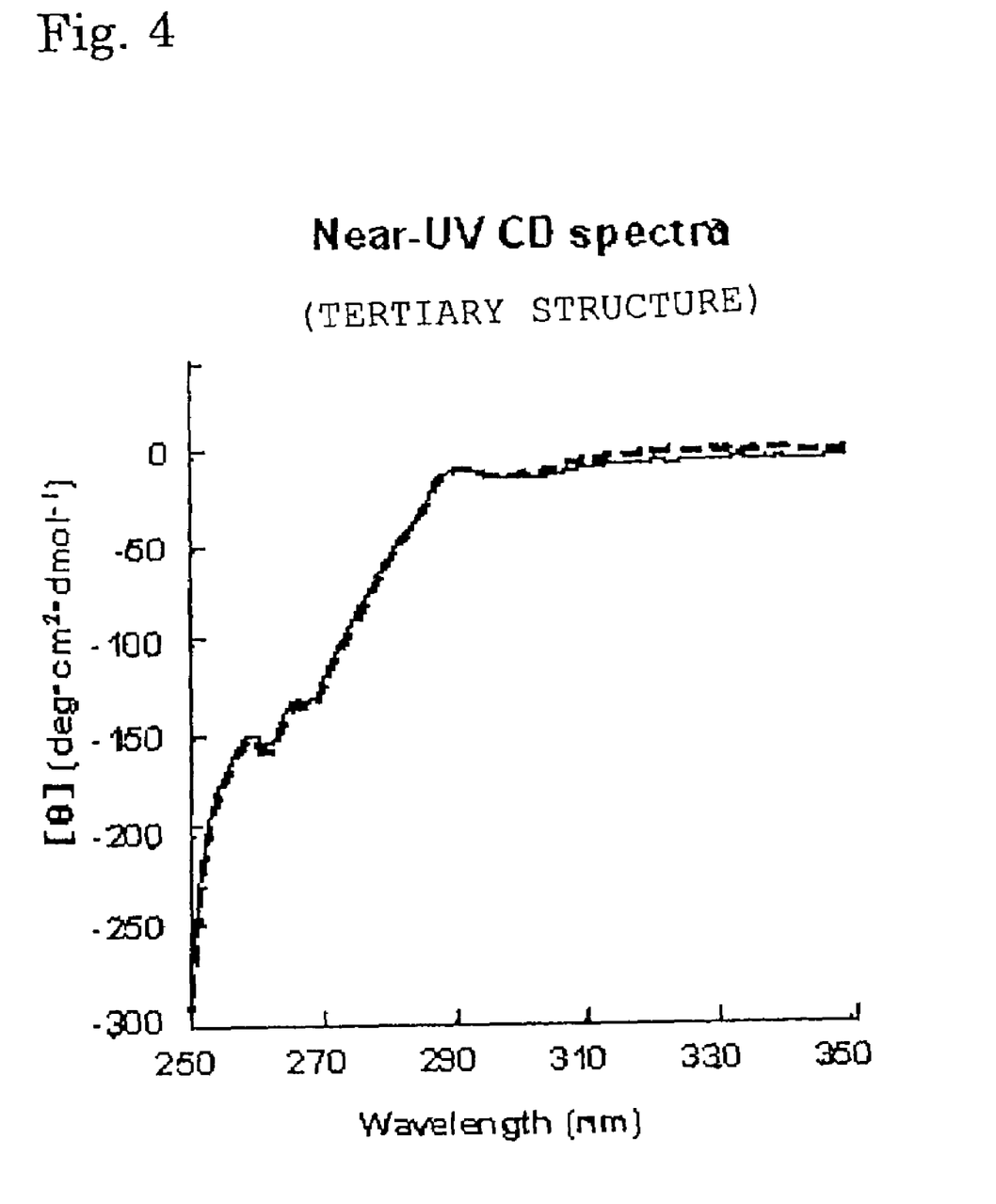
FIG. 4 is a graph illustrating the spectra of a nitroso-HSA sample in a near-ultraviolet region (Near-UV CD spectra).

In FIG. 4, the ordinate axis indicates [θ], that is, ellipticity per mole and the horizontal axis indicates wavelength. The abscissa axis indicates wavelength. HSA indicated by a broken line indicates non-nitrosylated albumin and S-NO-HSA indicated by a solid line indicates nitroso-HSA sample.

FIG. 3 indicates that the nitroso-HSA sample in a far-ultraviolet region that reflects a secondary structure exhibited substantially the same CD-spectrum as that of HSA, thus confirming that the sample maintained the inherent a-helix structure of albumin.

In addition, FIG. 4 indicates that the nitrosoalbumin sample in a near-ultraviolet region, which reflects a tertiary structure, exhibited substantially the same CD-spectrum as that of HSA. As mentioned-above, the nitroso-HSA sample obtained in Example 3 maintained the original structure of HSA.

Experimental Example 2

The S-nitroso-HSA sample obtained in Example 2 was subjected to low temperature sterilization at 60° C. for 10 hours. The S-nitroso-HSA sample after the low temperature sterilization treatment was confirmed as to whether or not the protein was aggregated in the presence or absence of dithiothreitol (hereinafter, abbreviated as DTT) by SDS polyacrylamide gel electrophoresis (hereinafter, abbreviated as SDS-PAGE). The result obtained is illustrated in FIG. 5.

Figure 5:
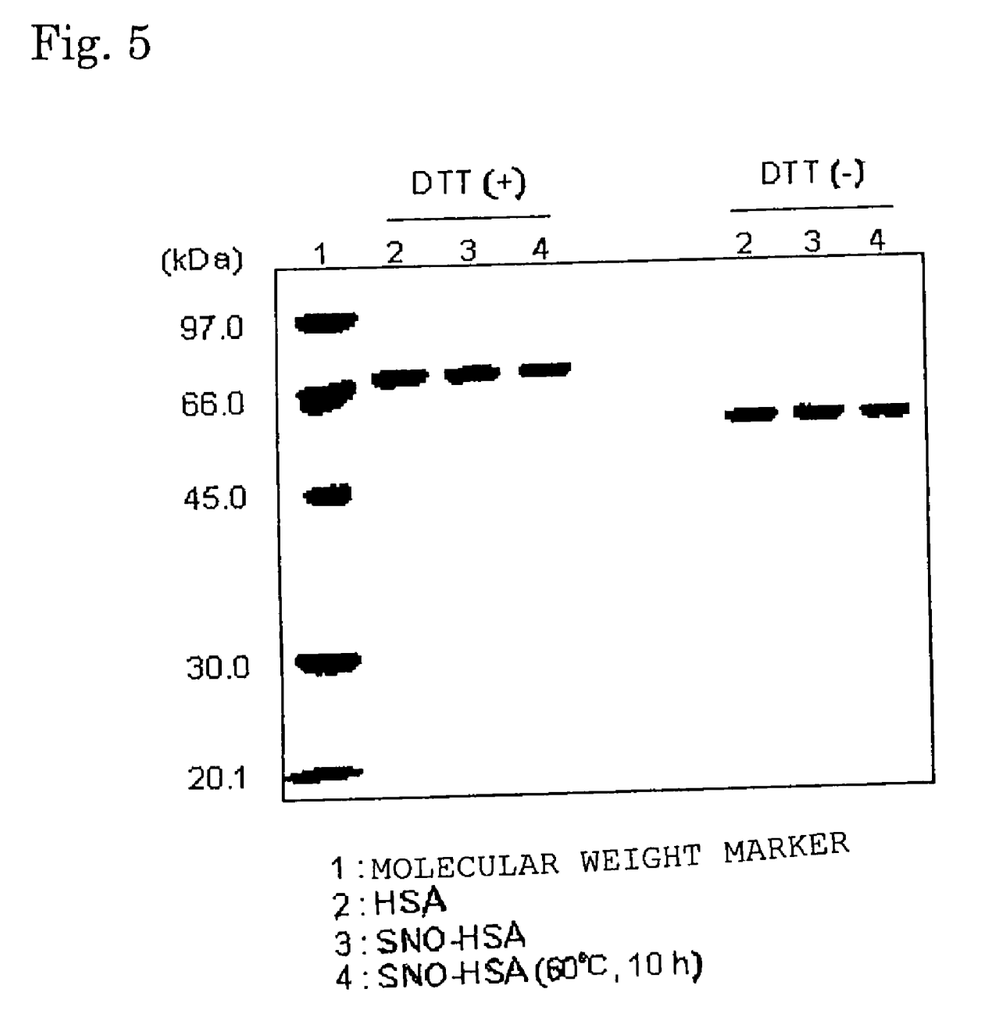
FIG. 5 illustrates a band of SDS-PAGE electrophoresis of an S-nitroso-HSA sample after low temperature sterilization treatment.

In FIG. 5, "1: Molecular weight marker" indicates a trypsin inhibitor (molecular weight: 20,100), carbonic anhydrase (molecular weight: 30,000), ovalbumin (molecular weight: 45,000), albumin (molecular weight: 66,000), and phosphorylase b (molecular weight: 97,000) as molecular weight markers. "2: HSA" indicates a non-nitrosylated albumin. "3: S-NO-HSA" indicates an S-nitroso-HSA sample. "4: S-NO-HSA (60° C., 10 h)" indicates a nitroso-HSA sample after a low temperature sterilization treatment.

The nitroso-HSA sample after the low temperature sterilization treatment did not show aggregation like HSA and nitroso-HSA (hereinafter, abbreviated as S-NO-HSA). That is, the nitroso-HSA sample was stable even against low temperature sterilization.

Experimental Example 3

Nitroso-HSA sample obtained in Example 2 was evaluated using an ischemia reperfusion injury model obtained by median incision of the abdomen of a rat under etherization to expose the liver, simultaneously clipping the portal vein and hepatic artery so that only the middle lobe and left lobe were ischemic to block the blood flow for 45 minutes and then recovering the blood flow. As the evaluation, after 60 minutes, AST induced and plasma level of AST were measured.

That is, after the reperfusion, 0.1 mmol/kg or 0.5 mmol/kg of the nitroso-HSA sample obtained in Example 2 was separately and immediately intravenously administered. For comparison, 0.5 mmol/kg HSA was separately administered in the same manner as above. The result obtained is illustrated in FIG. 6.

Figure 6:
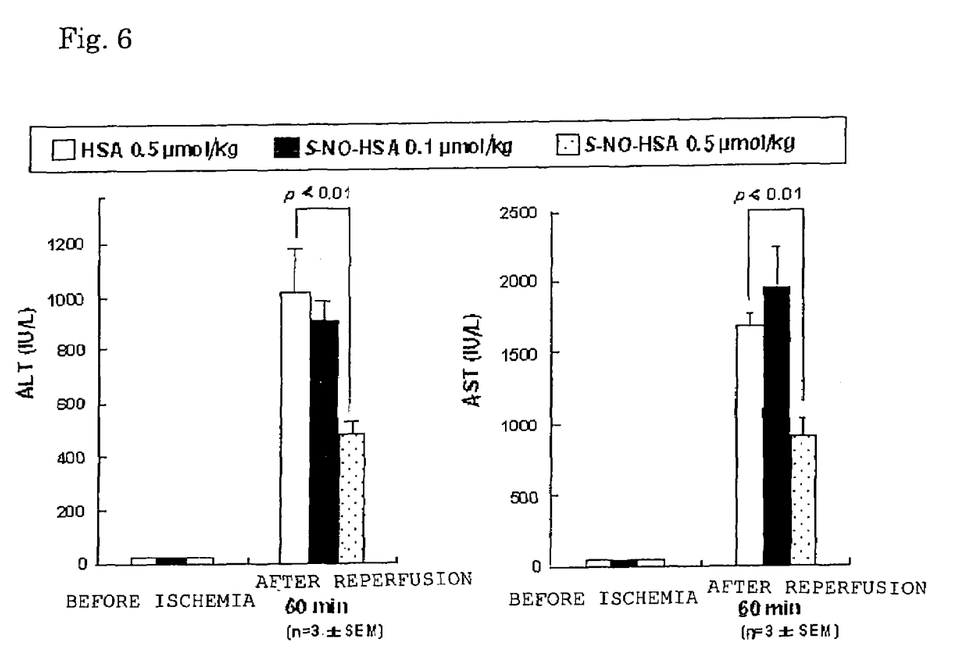
FIG. 6 shows charts illustrating variation of levels of ALT and AST of a nitroso-HSA sample after low temperature sterilization treatment before ischemia and after reperfusion in rats.

In the ordinate axes in FIG. 6, ALT indicates the amount of alanine-amino group transferase while AST indicates the amount of aspartic acid-amino group transferase. HSA 0.5 mmol/kg expressed by a white bar indicates administration with a 0.5 mmol/kg non-nitrosylated albumin; S-NO-HSA 0.1 mmol/kg expressed by a black bar indicates administration with a 0.1 mmol/kg nitroso-HSA sample; and S-NO-HSA. 0.5 mmol/kg expressed by a bar with dots indicates administration with a 0.5 mmol/kg nitroso-HSA sample.

FIG. 6 indicates that in the group administered with the 0.5 mmol/kg nitroso-HSA sample, increases in alanine-amino group transferase value (hereinafter, abbreviated as ALT value) and asparagine-amino group transferase value (hereinafter, abbreviated as AST value), respectively, were significantly suppressed as compared with the group administered with HSA. This indicates that the nitroso-HSA sample had an effect on the liver ischemia reperfusion injury.

This application claims priority of Japanese patent application No. 2006-227427 filed Aug. 24, 2006, which is incorporated herein by reference.

What is claimed is:

1. A method of producing an S-nitrosoalbumin, comprising adding a nitrogen monoxide donor to a solution of an albumin containing a stabilizing agent comprising at least one compound or a combination of compounds selected from an N-acetylamino acid, a fatty acid and a fatty acid salt to produce the S-nitrosoalbumin.

2. The production method according to claim 1, wherein the N-acetyl amino acid is N-acetyltryptophane or N-acetylmethionine.

3. The production method according to claim 1, wherein the fatty acid is oleic acid or caprylic acid.

4. The production method according to claim 1, wherein the fatty acid salt is sodium caprylic acid.

5. The production method according to claim 1, wherein the nitrogen monoxide donor is S-nitrosoglutathione.

* * * * *